United States Patent [19]

Harper et al.

[11] Patent Number: 5,594,028
[45] Date of Patent: Jan. 14, 1997

[54] ANTI-TUMOR METHOD AND COMPOUNDS

[75] Inventors: Richard W. Harper; J. Jeffry Howbert, both of Indianapolis; Gerald A. Poore, Martinsville; Brent J. Rieder, Greenfield; Eddie V. P. Tao; James A. Aikins, both of Indianapolis, all of Ind.

[73] Assignee: Eli Lilly and Company, Indianapolis, Ind.

[21] Appl. No.: 343,056

[22] Filed: Nov. 21, 1994

Related U.S. Application Data

[62] Division of Ser. No. 223,807, Apr. 6, 1994, abandoned, which is a continuation of Ser. No. 858,816, Mar. 27, 1992, abandoned, which is a division of Ser. No. 351,755, May 15, 1989, Pat. No. 5,116,874, which is a continuation of Ser. No. 49,185, May 12, 1987, abandoned, which is a continuation-in-part of Ser. No. 888,675, Jul. 24, 1986, abandoned, which is a continuation-in-part of Ser. No. 779,354, Sep. 23, 1985, abandoned.

[51] Int. Cl.$^6$ .......................... A61K 31/36; A61K 31/18; C07C 311/16; C07D 307/79
[52] U.S. Cl. .......................... 514/464; 514/415; 514/456; 514/469; 514/592; 548/469; 548/503; 549/362; 549/366; 549/434; 549/462; 549/467; 564/36
[58] Field of Search .................. 564/36; 514/592, 514/456, 464, 469, 415; 549/362, 366, 434, 462, 467; 548/469, 503

[56] References Cited

U.S. PATENT DOCUMENTS

| | | | |
|---|---|---|---|
| 3,083,207 | 3/1963 | Hoehn et al. | 548/503 XK |
| 3,097,240 | 7/1963 | Aumuller | 260/553 |
| 3,097,241 | 7/1963 | Korger et al. | 260/553 |
| 3,097,242 | 7/1963 | Hoehn et al. | 260/553 |
| 3,102,115 | 8/1963 | Breuer et al. | 548/503 XK |
| 3,102,121 | 8/1963 | Breuer et al. | 549/51 |
| 3,418,367 | 12/1968 | Dietrich | 564/39 |
| 3,849,110 | 11/1974 | Soper et al. | 71/103 |
| 4,276,290 | 6/1981 | Weir et al. | 424/200 |
| 4,659,709 | 4/1987 | Harada et al. | 514/229 |
| 4,845,128 | 7/1989 | Harper et al. | 514/592 |
| 5,116,874 | 5/1992 | Poore | 514/592 |
| 5,254,582 | 10/1993 | Bodor et al. | 514/469 |

FOREIGN PATENT DOCUMENTS

| | | | |
|---|---|---|---|
| 1208561 | 7/1986 | Canada | A61K 31/17 |
| 93622 | 6/1958 | Denmark | 564/39 |
| 99339 | 1/1984 | European Pat. Off. | A01N 47/36 |
| 107214 | 5/1984 | European Pat. Off. | |
| 123303 | 10/1984 | European Pat. Off. | C07C 405/12 |
| 166615 | 1/1986 | European Pat. Off. | A61K 31/64 |
| 1144259 | 5/1956 | Germany . | |
| 1159937 | 12/1963 | Germany . | |
| 1240866 | 5/1967 | Germany . | |

OTHER PUBLICATIONS

Breuer, et al., *Chimie Therapeutique*, 659 (1973).
Lerner, et al., *Metabolism*, 14 (5), 578 (1965).
Marshall, et al., *J. Org. Chem.*, 23, 927 (1958).
Marshall, et al., *J. Med. Chem.*, 6, 60 (1963).
Shah, et al., *J. Med. Chem.*, 12, 938 (1969).
F. Kurzer, *Chem. Rev.*, 50, 1 (1952).
Chemical Abstract 71:11457w (1969).
G. F. Holland, et al., *J. Med. Pharm. Chem.*, 3(1), 99 (1961).
T. P. Gandhi, et al., *Arzneim.–Forsch.*, 21, 968 (1971).
P. Rajasopalan, et al., *J. Org. Chem.*, 30, 3369 (1965).
S. Peterson, *Chem. Ber.*, 83, 551 (1950).
E. Haack, *Arzneim.–Forsch.*, 8, 444 (1958).
S. Onisi, *J. Pharm. Soc. Japan*, 79, 632 (1959).
S. Onisi, *J. Pharm. Soc. Japan*, 79, 559 (1959).
H. Ruschig, et al., *Arzneim.–Forsch.*, 8, 448 (1958).
T. P. Gandhi, et al., *Arzneim.–Forsch.*, 21, 961 (1971).
Proceedings of the AACR, vol. 28, p. 309 (Mar., 1987).
Derwent Abstract 85–200307/33 (1985).

*Primary Examiner*—Shailendra Kumar
*Attorney, Agent, or Firm*—Robert D. Titus; Joseph A. Jones

[57] ABSTRACT

This invention provides certain sulfonamide derivatives, their pharmaceutical formulations, and their use in the treatment of susceptible neoplasms in mammals.

4 Claims, No Drawings

ANTI-TUMOR METHOD AND COMPOUNDS

This application is a division of application Ser. No. 08/223,807 filed on Apr. 6, 1994, now abandoned, which is a continuation of application Ser. No. 07/858,816 filed on Mar. 27, 1992, now abandoned, which was a division of application Ser. No. 07/351,755 filed on May 15, 1989, now U.S. Pat. No. 5,116,874, which was a continuation of application Ser. No. 07/049,185 filed May 12, 1987, now abandoned, which was a continuation-in-part of application Ser. No. 06/888,675, filed Jul. 24, 1986, now abandoned, which was a continuation-in-part of application Ser. No. 06/779,354, filed Sep. 23, 1985, now abandoned.

BACKGROUND OF THE INVENTION

Despite the development of numerous chemical agents and sophisticated regimens of drug therapy, the ravages of cancer continue to extract an ever-increasing human toll of suffering and death. Although many advances have been made, especially in the area of combination drug therapy, the need for new and better methods of treating neoplasms and leukemias has not diminished. This is especially evident in the area of inoperable or metastatic solid tumors, such as various forms of lung cancer.

To be especially useful, new chemotherapeutic agents should have a wide spectrum of activity, a large therapeutic index, and be chemically stable and compatible with other agents. In addition, any new agents having oral activity would be especially useful so that initial treatment and subsequent maintenance therapy would be made easily and without inconvenience or pain to the patient.

We have discovered a series of sulfonylureas which are useful in the treatment of solid tumors. The compounds are orally active and relatively non-toxic providing an excellent therapeutic index.

Many sulfonylureas are known in the art. Compounds such as 1-(4-halo- and 4-methyl-phenyl)-3-[phenyl-and (4-chloro-, 4-bromo-, and 4-methyl-phenyl-)sulfonyl]urea are taught in Chemical Abstracts 71:11457w (1969), Holland, et al., *J. Med. Pharm. Chem.*, 3 (1), 99 (1961), Gandhi, et al., *Arzneim.-Forsch.*, 21, 968 (1971), Rajagopalan, et al., *J. Org. Chem.*, 30, 3369 (1965), and Petersen, *Chem. Ber.*, 83, 551 (1950). In general, these compounds are taught to have oral hypoglycemic activity. In addition, some antimycotic activity is noted and the compounds have also been prepared as derivatives of carbodiimides. A general review of compounds of this structural type is taught by Kurzer, *Chem. Rev.*, 50, 1 (1952). Bicyclic sulfonylureas are also known in the art as hypoglycemic agents; see, e.g., Chemical Abstracts 67:54036t (abstracting German OLS 1,249,866), U.S. Pat. No. 3,097,242, Chemical Abstracts 60:9220h (abstracting German OLS 1,159,937), and Lerner, et al., *Metab., Clin. Exptl.*, 14(5), 578 (1965). No anti-tumor activity is disclosed or inferred in any of the above references.

SUMMARY OF THE INVENTION

This invention provides sulfonylurea derivatives of the formula

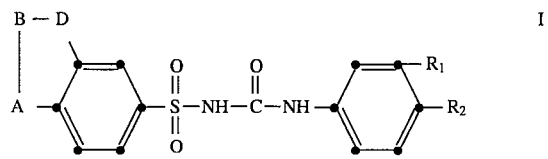

wherein A is —O—, —S(O)$_n$—, —CH$_2$S(O)$_n$—, —NR—, —CH$_2$—, —CH$_2$CH$_2$—, or —CH$_2$O—;

D is —CH$_2$—, —S(O)$_n$—, —NR—, —CH$_2$S(O)$_n$—, or —O—;

B is —CH$_2$, —O—, —S(O)$_n$—, or —NR—;

R is methyl or ethyl;

R$_1$ is hydrogen or halo;

R$_2$ is halo or trifluoromethyl;

n is 0–2;

provided that:
 B is a group other than —CH$_2$— only when A and D are both —CH$_2$CH$_2$— or —CH$_2$—; and
 D is —CH$_2$S(O)$_n$— only when A is —O—, —S(O)$_n$—, —NR— or —CH$_2$—.

This invention also provides a method of treating susceptible neoplasms in mammals which comprises administering to a mammal in need of such treatment an effective amount of a compound of this invention.

In addition, this invention provides pharmaceutical formulations comprising a compound of formula I in combination with a suitable pharmaceutical carrier, diluent, or excipient. These formulations are particularly useful in treating mammals suffering from susceptible neoplasms.

DETAILED DESCRIPTION AND PREFERRED EMBODIMENTS

The term "halo" refers to fluoro, chloro, bromo, and iodo. The term "C$_1$–C$_3$ alkyl" refers to methyl, ethyl, propyl, and isopropyl.

The preferred compounds used in the method of this invention are those of Formula I wherein a) R$_1$ is hydrogen, b) R$_2$ is halo, especially bromo, chloro, or fluoro, or trifluoromethyl, c) A and B are —CH$_2$—; and d) D is —CH$_2$— or —O—.

Another preferred group of compounds comprises those of Formula I wherein A is —O—, —NCH$_3$—, —CH$_2$—, —CH$_2$CH$_2$—, or —CH$_2$O—; D is —CH$_2$— or —O—; B is —CH$_2$—; R$_1$ is hydrogen or halo; and R$_2$ is halo or trifluoromethyl. Additionally preferred are the compounds of this group wherein A and D independently are —S(O)$_n$— or —CH$_2$S(O)$_n$— as well as the preceding groups.

Still another particularly preferred group of compounds comprises those of Formula I wherein A is —CH$_2$— or —CH$_2$CH$_2$—; D and B are —CH$_2$—; R$_1$ is hydrogen or halo; and R$_2$ is halo or trifluoromethyl.

Another preferred group of compounds are those wherein A is —CH$_2$—, —O— or —NR—; B is —CH$_2$—; D is —CH$_2$— or —O—; R$_1$ is hydrogen; and R$_2$ is halo or trifluoromethyl, especially chloro or bromo.

The most preferred compound of this invention is N-([(4-chlorophenyl)amino]carbonyl)-2,3-dihydro-1H-indene-5-sulfonamide.

The compounds of formula I are generally referred to as derivatives of N-([(substituted phenyl)-amino]carbonyl)arylsulfonamides, for example as used in the previous paragraph. Alternatively, the compounds are referred to as 1-(substituted phenyl)-3-(arylsulfonyl)ureas.

The compounds of formula I may be prepared by any number of methods known in the literature. These methods are generally summarized by Kurzer, *Chem. Rev.*, 50, 1 (1952), especially pages 4–19. Specific references describing processes that can be employed in the preparation of compounds of formula I are those previously described in the "Background of the Invention" section above. All of the above references are expressly incorporated into this application by reference.

A preferred method of preparing the compounds of formula I is that of the reaction of a sulfonylisocyanate of the formula II

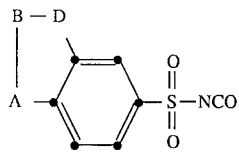

with an aniline derivative of the formula III

where A, B, D, $R_1$, and $R_2$ are the same as previously defined.

The reaction between compounds II and III is usually performed using equimolar amounts of the two reactants, although other ratios are operative. The reaction is best carried out in an aprotic non-reactive solvent such as benzene, toluene, acetonitrile, diethyl ether, tetrahydrofuran, dioxane, or preferably methylene chloride. The reaction may be carried out at temperatures from about 0° C. up to the boiling point of the reaction mixture. At the preferred temperature range of about 20°–30° C., the reaction produces a strong exotherm and the reaction is usually complete within 1 hour. The product thus obtained is recovered by filtration and may be purified, if desired, by any number of methods known to those skilled in the art, such as chromatography or crystallization.

Alternatively, an appropriately substituted sulfonamide IV

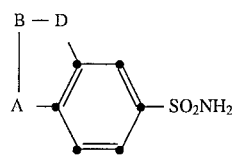

may be reacted with an isocyanate of the formula V

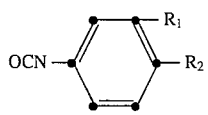

to provide the compounds of Formula I. The reaction is generally carried out in a water miscible, non-reactive solvent such as tetrahydrofuran or acetone. Generally, an equimolar amount or slight molar excess of V is employed, although other ratios are operative. In addition, an aqueous solution of a base, such as sodium or potassium hydroxide, is employed. Usually the amount of base used is approximately equimolar to the amount of IV. The reaction is generally carried out from about 0° C. up to the boiling point of the reaction mixture. At the preferred temperature range of 20°–30° C., the reaction is usually complete within about three days.

The preferred method of preparing compounds of Formula I involves the reaction of sulfonamide IV with an alkyl haloformate to provide carbamate VI which is then reacted with aniline III to provide the corresponding product I

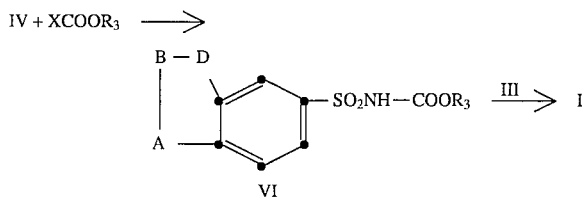

where X is bromo or chloro and $R_3$ is $C_1$–$C_3$ alkyl. The transformation of IV into VI is usually accomplished in a non-reactive solvent, such as acetone or methyl ethyl ketone, in the presence of an acid scavenger, such as an alkali metal carbonate, for example potassium carbonate. A molar excess of the haloformate is usually added, although other ratios are operative, and the reaction mixture heated at a temperature from about 30° C. up to the reflux temperature for a period of 1–6 hours to provide the desired intermediate VI. Intermediate carbamate VI and aniline III are then heated together in an inert high-boiling solvent, such as dioxane, toluene, or diglyme, at temperatures from about 50° C. up to the reflux temperature of the mixture to provide the desired product I.

Intermediates II, III, IV, and V and any other reagents required for other methods of preparation, are either commercially available, are known in the literature, or can be prepared by methods known in the art.

Certain intermediates of Formula IV, especially those wherein A and D are independently —S(O)$_n$—, —CH$_2$S(O)$_n$—, —O— or —CH$_2$—, may be prepared according to the process taught in copending U.S. application Ser. No. 889,141, filed Jul. 23, 1986. This process involves chlorosulfonating an appropriately substituted benzene compound at 50°–130° C. with a Villsmeier reagent prepared from sulfuryl chloride and dimethylformamide followed by ammonolysis with ammonia or ammonium hydroxide. Examples 7A and 8 below are illustrative of this process.

Intermediates wherein A or D are —SO—, —SO$_2$—, —CH$_2$SO— or —CH$_2$SO$_2$— are prepared by oxidizing the sulfur atoms with a conventional oxidizing agent, such as perbenzoic acid. Compounds wherein both A and D are sulfur-containing moieties, and are in different oxidation states, are prepared by carrying out the oxidation under mild conditions and separating the resulting mixture of products. For example, the oxidation may be carried out at low temperatures and in the presence of low concentrations of oxidizing agent to achieve mild oxidation conditions.

The following examples further illustrate the preparation of the compounds of this invention. The examples are illustrative only and are not intended to limit the scope of the invention in any way.

EXAMPLE 1

N-([(4-chlorophenyl)amino]carbonyl)-2,3-dihydro-1H-indene-5-sulfonamide

To a solution of 93.2 g of 2,3-dihydro-5-indenylsulfonamide in 300 ml of acetone were added 490 ml of a 1N sodium hydroxide solution. A solution of 79.36 g of 4-chlorophenylisocyanate in 250 ml of acetone was added to the reaction mixture with stirring. After stirring at room temperature for 18 hours, the reaction mixture was filtered and 490 ml of 1N hydrochloric acid were added to the filtrate thereby providing a fine white precipitate. One liter of water was added, and the solid was recovered by filtration to provide 144.86 g of the desired title product, m.p. 169°–172° C.

Analysis for $C_{16}H_{15}ClN_2O_3S$:
Calculated: C, 54.78; H, 4.31; N, 7.79;
Found: C, 54.95; H, 4.43; N, 7.94.

EXAMPLE 2

N-([(4-chlorophenyl)amino]carbonyl)-5,6,7,8-tetrahydro-2-naphthalene sulfonamide The title compound was prepared by the method of Example 1 in 56% yield from 5,6,7,8-tetrahydro-2-naphthalenesulfonamide and 4-chlorophenylisocyanate, m.p. 163°–165° C.

Analysis for $C_{17}H_{17}ClN_2O_3S$:
Calculated: C, 55.96; H, 4.70; N, 7.68; S, 8.79;
Found: C, 55.91; H, 4.62; N, 7.56; S, 9.00.

EXAMPLE 3

Alternate preparation of N-([(4-chlorophenyl)amino]carbonyl)-2,3-dihydro-1H-indene-5-sulfonamide A. Preparation of [(2,3-dihydro-1H-inden-5-yl)sulfonyl] carbamic acid ethyl ester.

Two hundred eighty grams of potassium carbonate were added to a solution of 181.4 g of 2,3-dihydro-5-indenylsulfonamide in three liters of methyl ethyl ketone. The suspension was stirred for 45 minutes at which time 98 ml of ethyl chloroformate were added in dropwise manner. After stirring for one hour at room temperature, the mixture was heated to reflux and stirred an additional three hours. After cooling, the mixture was added to ice water, filtered, brought to a pH of 1, and extracted three times with ethyl acetate. The combined organic extracts were washed with water and a saturated sodium chloride solution, dried over sodium sulfate, and evaporated to dryness in vacuo. Crystallization of the residue from toluene provided 176.2 g of the desired subtitle intermediate, m.p. 92°–95° C.

Analysis for $C_{12}H_{15}NO_4S$:
Calculated: C, 53.52; H, 5.61; N, 5.20;
Found: C, 53.76; H, 5.71; N, 5.08.

B. Preparation of N-([(4-chlorophenyl)amino]carbonyl)-2,3-dihydro-1H-indene-5-sulfonamide.

A solution of 2.69 g of [(2,3-dihydro-1H-inden-5-yl)sulfonyl]carbamic acid ethyl ester and 1.27 g. of 4-chloroaniline in 50 ml of dioxane was heated at reflux for 16 hours under a nitrogen atmosphere. The solution was added to water and extracted with ethyl acetate. The organic extract was dried over sodium sulfate and concentrated in vacuo giving a crystalline solid. The solid was triturated with toluene and filtered to provide 1.6 g of the desired title product, m.p. 175°–177° C.

Analysis for $C_{16}H_{15}ClN_2O_3S$:
Calculated: C, 54.78; H, 4.31; N, 7.79;
Found: C, 54.63; H, 4.47; N, 7.84.

EXAMPLE 4

N-{[(4-chlorophenyl)amino]carbonyl}-2,3-dihydro-5-benzofuransulfonamide

The title product was prepared in 26.1% yield from 2,3-dihydro-5-benzofuransulfonamide and 4-chlorophenylisocyanate following the procedure of Example 1, m.p. 190°–194° C.

Analysis for $C_{15}H_{13}ClN_2O_4S$:
Calculated: C, 51.07; H, 3.71; N, 7.94; S, 9.07;
Found: C, 51.32; H, 4.00; N, 7.73; S, 9.02.

EXAMPLE 5

N-{[(4-chlorophenyl)amino]carbonyl}-2,3-dihydro-1-methyl-1H-indole-5-sulfonamide Following the procedure of Example 3B, the title product was prepared in 60% yield from [(2,3-dihydro-1-methyl-1H-indol-5-yl)sulfonyl]carbamic acid ethyl ester and 4-chloroaniline, m.p. 145°–147° C.

Analysis for $C_{16}H_{16}ClN_3O_3S$:
Calculated: C, 52.53; H, 4.41; N, 11.49; S, 8.76;
Found: C, 52.78; H, 4.47; N, 11.19; S, 8.56.

EXAMPLE 6

N-{[(3,4-dichlorophenyl)amino]carbonyl}-2,3-dihydro-1H-indene-5-sulfonamide

A solution of 2.67 g of 3,4-dichloroaniline in 10 ml of toluene was added to 3.87 g of 2,3-dihydro-5-indenylsulfonylisocyanate in 20 ml of toluene. After stirring 7 hours, the resulting precipitate was recovered by filtration, washed with toluene and dried providing 5.38 g of the title product, m.p. 155.5°–158° C.

Analysis for $C_{16}H_{14}Cl_2N_2O_3S$:
Calculated: C, 49.88; H, 3.66; N, 7.27; S, 8.32;
Found: C, 50.13; H, 3.84; N, 7.31; S, 8.05.

EXAMPLE 7

N-{[(4-chlorophenyl)amino]carbonyl}-1,3-benzodioxole-5-sulfonamide

A. Preparation of 1,3-benzodioxole-5-sulfonamide.

A 500 ml 3-neck round bottom flask was charged with 38.7 g (0.52 mole) of dimethylformamide. The contents of the flask were cooled to 0° C. After cooling, 70.18 g (0.52 mole) of sulfuryl chloride were added and the contents of the flask stirred for 10 minutes while maintaining the temperature at approximately 10° C.

After the Villsmeier reagent was formed, 61.06 g (0.5 mole) of 1,3-benzodioxole were added over a period of 5 minutes. The mixture was heated to 80° C. for approximately 10 minutes. The temperature was increased to 110° C., and maintained for 5 minutes. The reaction mixture was allowed to cool to 40° C. and poured into a mixture of 450 g crushed ice, 200 ml water, and 200 ml of chloroform.

The resulting organic layer was decanted and then dripped into 200 ml of concentrated ammonium hydroxide. The solution was stirred for approximately 1½ hours. After stirring, the organic and aqueous phases were allowed to separate and a yellow granular precipitate formed at the interface of the two layers. This solid was collected by filtration, washed with 100 ml of water, and dried overnight at 40° C. to provide 26.9 g of the desired subtitle intermediate, m.p. 158°–160° C. Both mass spectroscopy and NMR spectra were consistent with the structure of the desired intermediate.

B. Preparation of N-{[(4-chlorophenyl)amino]carbonyl}-1,3-benzodioxole-5-sulfonamide.

The title product was prepared in 75% yield from the intermediate of Example 7A and 4-chlorophenylisocyanate following the procedure of Example 1.

Analysis for $C_{14}H_{11}ClN_2O_5S$:
    Calculated: C, 47.40; H, 3.13; N, 7.90;
    Found: C, 47.54; H, 3.23; N, 8.10.

EXAMPLE 8

N-{[(4-Chlorophenyl)amino]carbonyl}-2,3-dihydro-1,4-benzodioxin-6-sulfonamide

Following the procedure of Example 7A, 1,4-benzodioxan was transformed into 1,4-benzodioxan-6-sulfonamide in 34% yield. This sulfonamide was then converted into the title sulfonylurea in 66% yield according to the procedure of Example 1, m.p. 191° C.

Analysis for $C_{15}H_{13}ClN_2O_5S$:
    Calculated: C, 48.85; H, 3.55; N, 7.60;
    Found: C, 48.57; H, 3.75; N, 7.40.

The compounds of formula I have been shown to be active against transplanted mouse tumors in vivo. The compounds are active in the test systems when administered according to a variety of dosage schedules. In general, the compounds were administered orally daily or twice daily for 8–10 days.

To demonstrate the anti-tumor activity of the compounds of Formula I, the compounds were tested in animals bearing a 6C3HED lymphosarcoma, also known as the Gardner lymphosarcoma (GLS). Table 1 gives the results of several experiments in mice bearing this tumor when compounds were administered orally. In the Table, column 1 gives the example number of the compound; column 2, the dose level; and column 3, the percent inhibition of tumor growth. The results are the average of 10 animals per group as compared with a suitable control group.

TABLE 1

Activity of the Compounds of Formula I
Against the 6C3HED Lymphosarcoma*

| Compound of Example No. | Dose** | Percent Inhibition |
|---|---|---|
| 1 | 150 | 91 |
|   | 300 | 99 |
|   | 50 twice daily | 65 |
|   | 75 twice daily | 89 |
|   | 100 twice daily | 93 |
|   | 150 twice daily | 100 |
|   | 200 twice daily | 99 |
|   | 300 twice daily | 100 |
|   | 400 twice daily | 100 |
| 2 | 150 | 38 |
|   | 300 | 78 |
| 4 | 150 | 71 |
|   | 300 | 94 |
| 5 | 150 | 71 |
|   | 300 | 100 |
| 6 | 150 | 74 |
|   | 300 | 97 |
| 7 | 150 | 85 |
|   | 300 | 100 |
| 8 | 150 | 38 |
|   | 300 | 49 |

*Tested in C3H mice.

TABLE 1-continued

Activity of the Compounds of Formula I
Against the 6C3HED Lymphosarcoma*

| Compound of Example No. | Dose** | Percent Inhibition |
|---|---|---|

**mg/kg administered orally in emulphor. Dosing began the day following inoculation. Compounds were dosed once every day for eight days, except where noted.

In addition, one of the compounds of Formula I was tested orally in additional test systems. These include the subcutaneous B-16 melanoma (B16-sc), the X5563 plasma cell myeloma (X5563), the M-5 ovarian carcinoma (M-5), the C3H mammary carcinoma (C3H), colon carcinoma-26 (C6), the CA-755 adenocarcinoma (CA755), the Madison Lung Carcinoma (Madison), the P388 lymphocytic leukemia (P388), and the Lewis Lung carcinoma (LL). A summary of these test results is provided in Table 2.

TABLE 2

Activity of Compound 1 against
a variety of tumor models

| Compound of Example No. | Tumor | Dose* | Percent Inhibition |
|---|---|---|---|
| 1 | CA755 | 37.5 | 30 |
|   |       | 75.0 | 67 |
|   |       | 150  | 91 |
|   |       | 300  | 99 |
|   | LL    | 37.5 | 4 |
|   |       | 75   | 36 |
|   |       | 150  | 37 |
|   |       | 300  | 58 |
|   | C6    | 37.5 | 24 |
|   |       | 75.0 | 36 |
|   |       | 150  | 69 |
|   |       | 300  | 85 |
|   |       | 600  | 100 |
|   | M-5   | 37.5 | 53 |
|   |       | 75.0 | 76 |
|   |       | 150  | 88 |
|   |       | 300  | 96 |
|   |       | 600  | 99 |
|   | Madison | 37.5 | 44 |
|   |       | 75.0 | 55 |
|   |       | 150  | 61 |
|   |       | 300  | 80 |
|   | X5563** | 37.5 | 0–38 |
|   |       | 75   | 38–41 |
|   |       | 150  | 50–54 |
|   |       | 300  | 46–66 |
|   | C3H   | 37.5 | 49 |
|   |       | 75   | 90 |
|   |       | 150  | 96 |
|   |       | 300  | 100 |
|   | P388  | 12.5 | 10*** |
|   |       | 25   | 8*** |
|   |       | 50   | 13*** |
|   |       | 100  | 19*** |
|   |       | 200  | 51*** |
|   | B16-sc | 37.5 | 13 |
|   |       | 75   | 13 |
|   |       | 150  | 3 |
|   |       | 300  | 25 |

*mg/kg per dose administered orally in emulphor. Dosing began the day following inoculation. Compounds were dosed twice daily for 10 days.
**Summary of two experiments.
***percent prolongation of life.

The compounds of Formula I are antineoplastic agents and the invention provides a method of treating susceptible neoplasms. The method comprises administering a compound by various routes including the oral, rectal, transdermal, subcutaneous, intravenous, intramuscular, or intranasal routes, being usually employed in the form of a pharmaceutical composition. It is a special feature of these compounds that they are effective following oral administration. Such compositions are prepared in a manner well known in the pharmaceutical art and comprise at least one active compound. Accordingly, in addition to the novel compounds of Formula I, the invention also includes pharmaceutical compositions comprising as active ingredient a compound of Formula I associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates,-tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range. For example, dosages per day will normally fall within the range of about 0.5 to about 600 mg/kg of body weight. In the treatment of adult humans, the range of about 1 to about 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following formulation examples may employ as active compounds any of the compounds of Formula I. The examples are illustrative only and are not intended to limit the scope of the invention in any way.

EXAMPLE 9

Hard gelatin capsules are prepared using the following ingredients:

|  | Quantity (mg/capsule) |
|---|---|
| N-{[(4-trifluoromethylphenyl)-amino]carbonyl}-2,3-dihydro-1,4-benzodioxin-6-sulfonamide | 250 |
| Starch dried | 200 |
| Magnesium stearate | 10 |

The above ingredients are mixed and filled into hard gelatin capsules in 460 mg quantities.

EXAMPLE 10

A tablet formula is prepared using the ingredients below:

|  | Quantity (mg/tablet) |
|---|---|
| N-([(3-fluoro-4-trifluoro-methylphenyl)amino]carbonyl)-2,3-dihydro-1H-indene-5-sulfonamide | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 11

An aerosol solution is prepared containing the following components:

|  | Weight % |
|---|---|
| N-([(3-chloro-4-fluorophenyl)-amino]carbonyl)-5,6,7,8-tetrahydro-2-naphthalenesulfonamide | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 12

Tablets each containing 60 mg of active ingredient are made up as follows:

| N-([(4-chlorophenyl)amino]-carbonyl)-2,3-dihydro-1H-indene-5-sulfonamide | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 13

Capsules each containing 80 mg of medicament are made as follows:

| | |
|---|---|
| N-([(4-fluorophenyl)amino]-carbonyl)-2,3-dihydro-1H-indene-5-sulfonamide | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 14

Suppositories each containing 225 mg of active ingredient are made as follows:

| | |
|---|---|
| N-([(3,4-dichlorophenyl)amino]-carbonyl)-5,6,7,8-tetrahydro-2-naphthalenesulfonamide | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 15

Suspensions each containing 50 mg of medicament per 5 ml dose are made as follows:

| | |
|---|---|
| N-([(3,4-difluorophenyl)amino]-carbonyl)-2,3-dihydro-1H-indene-5-sulfonamide | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 16

Capsules each containing 150 mg of medicament are made as follows:

| | |
|---|---|
| N-([(4-chlorophenyl)amino]carbonyl)-2,3-dihydro-1H-indene-5-sulfonamide | 150 mg |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

EXAMPLE 17

Tablets containing 80 mg of medicament each are made as follows:

| | |
|---|---|
| N-([(4-chlorophenyl)amino]-carbonyl)-1,3-benzodithiole-5-sulfonamide | 80 mg |
| Starch | 40 mg |
| Microcrystalline cellulose | 40 mg |
| Polyvinylpyrrolidone (as 10% aqueous solution) | 5 mg |
| Magnesium Stearate | 1 mg |
| Talc | 2 mg |
| Total | 168 mg |

Process as described in Example 12 and compress into tablets weighing 168 mg each.

EXAMPLE 18

Capsules containing 100 mg each of medicament are made as follows:

| | |
|---|---|
| N-([(3,4-dibromophenyl)amino]-carbonyl)-1,3,4-trihydro-2-benzothiopyran-6-sulfonamide | 100 mg |
| Starch | 60 mg |
| Magnesium stearate | 5 mg |
| Microcrystalline cellulose | 60 mg |
| Total | 225 mg |

The ingredients are blended, passed through a sieve, and filled into hard gelatin capsules in 200 mg quantities.

EXAMPLE 19

Capsules containing 125 mg of medicament each are made as follows:

| | |
|---|---|
| N-([(4-fluorophenyl)amino]-carbonyl)-1,3-benzodithiole-5-sulfonamide, 1,3,3-trioxide | 125 mg |
| Starch | 50 mg |
| Microcrystalline cellulose | 70 mg |
| Talc | 5 mg |
| Total | 250 mg |

Process as described in Example 13 and fill into capsules containing 250 mg each.

EXAMPLE 20

Capsules containing 150 mg of medicament each are made as follows:

| | |
|---|---|
| N-([(4-iodophenyl)amino]-carbonyl)-1,4-benzodithian-6-sulfonamide, 1,1-dioxide | 150 mg |
| Starch | 40 mg |
| Microcrystalline cellulose | 50 mg |
| Magnesium stearate | 10 mg |
| Total | 250 mg |

Process as described in Example 13 and fill in 250 mg quantities.

EXAMPLE 21

Capsules containing 90 mg of medicament each are made as follows:

| | |
|---|---|
| N-([(3-chloro-4-trifluoromethylphenyl)amino]carbonyl)-1,3-benzodithian-7-sulfonamide, 1,3-dioxide | 90 mg |
| Starch | 55 mg |
| Microcrystalline cellulose | 52 mg |
| Talc | 3 mg |
| Total | 200 mg |

Process as described in Example 13 and fill in 200 mg quantities.

EXAMPLE 22

Capsules containing 100 mg of medicament each are made as follows:

| | |
|---|---|
| N-([(4-iodophenyl)amino]-carbonyl)-1-ethyl-3-methyl-2,3-dihydrobenzimidazole-5-sulfonamide | 100 mg |
| Starch | 50 mg |
| Microcrystalline cellulose | 45 mg |
| Magnesium stearate | 5 mg |
| Total | 200 mg |

Process as described in Example 13 and fill in 200 mg quantities.

EXAMPLE 23

Capsules containing 80 mg of medicament each are made as follows:

| | |
|---|---|
| N-([(3,4-dichlorophenyl)amino]-carbonyl)-3,4-dihydro-1H-2-benzopyran-7-sulfonamide | 80 mg |
| Starch | 40 mg |
| Microcrystalline cellulose | 50 mg |
| Magnesium Stearate | 5 mg |
| Total | 175 mg |

Process as described in Example 13 and fill in 175 mg quantities.

EXAMPLE 24

Capsules containing 50 mg of medicament each are made as follows:

| | |
|---|---|
| N-([(3,4-difluorophenyl)amino]-carbonyl)-1,3-dihydro-2-benzothiophene-5-sulfonamide | 50 mg |
| Starch | 25 mg |
| Microcrystalline cellulose | 22 mg |
| Magnesium stearate | 3 mg |
| Total | 100 mg |

Process as described in Example 13 and fill in 100 mg quantities.

EXAMPLE 25

Capsules containing 100 mg of medicament each are made as follows:

| | |
|---|---|
| N-([(3-bromo-4-trifluoromethylphenyl)amino]carbonyl)-2-methyl-1,3-dihydroisoindole-5-sulfonamide | 100 mg |
| Starch | 44 mg |
| Microcrystalline cellulose | 43 mg |
| Magnesium stearate | 3 mg |
| Total | 200 mg |

Process as described in Example 13 and fill in 200 mg quantities.

We claim:

1. A compound selected from the group consisting of:

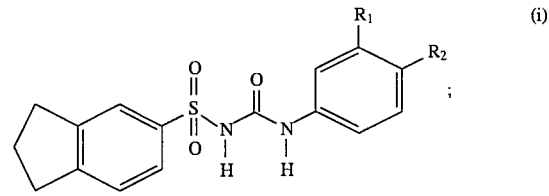

(i)

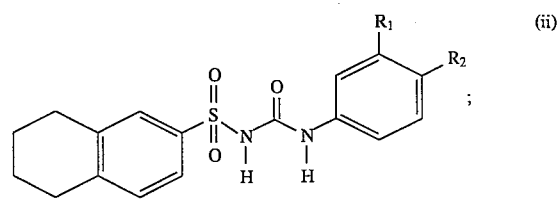

(ii)

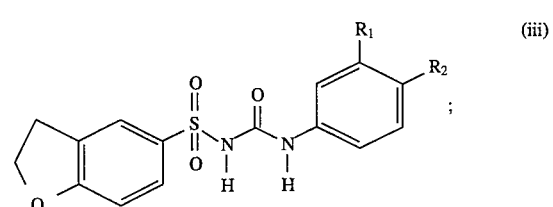

(iii)

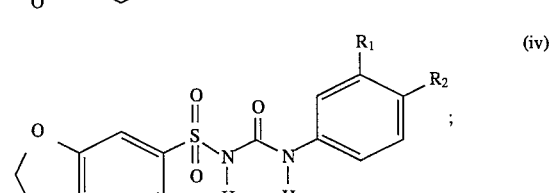

(iv)

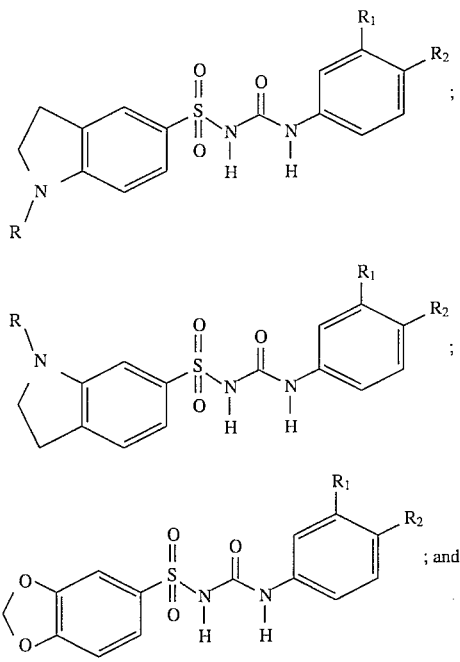

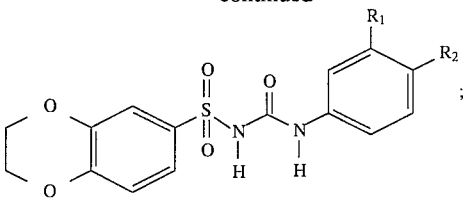

wherein

R is methyl or ethyl;

$R_1$ is hydrogen or halo; and $R_2$ is halo or trifluoromethyl;

provided that:

when the compound is of formula (i), (ii), (iii), (iv), (v), or (vi) and $R_2$ is halo; $R_1$ must be halo.

2. The compound of claim 1 which is N-{[(4-chlorophenyl)amino]carbonyl}-1,3-benzodioxole-5-sulfonamide.

3. A pharmaceutical formulation which comprises a compound of claim 1 and a pharmaceutically acceptable carrier or diluent.

4. A formulation according to claim 3 employing N-{[(4-chlorophenyl)amino]carbonyl}-1,3-benzodioxole-5-sulfonamide.

* * * * *